United States Patent
Ur

(10) Patent No.: US 10,078,842 B2
(45) Date of Patent: Sep. 18, 2018

(54) SELECTIVE SCENT DISPENSING

(71) Applicant: Shmuel Ur Innovation Ltd, Shorashim (IL)

(72) Inventor: Shmuel Ur, Shorashim (IL)

(73) Assignee: Shmuel Ur Innovation Ltd, Shorashim (IL)

( * ) Notice: Subject to any disclaimer, the term of this patent is extended or adjusted under 35 U.S.C. 154(b) by 152 days.

(21) Appl. No.: 15/120,280

(22) PCT Filed: Apr. 13, 2015

(86) PCT No.: PCT/IL2015/050394
§ 371 (c)(1),
(2) Date: Aug. 19, 2016

(87) PCT Pub. No.: WO2015/145453
PCT Pub. Date: Oct. 1, 2015

(65) Prior Publication Data
US 2017/0169436 A1    Jun. 15, 2017

(30) Foreign Application Priority Data
Mar. 24, 2014    (IL) .......................................... 231687

(51) Int. Cl.
*G05D 7/00* (2006.01)
*G06Q 30/00* (2012.01)
*G05B 15/02* (2006.01)
*A61L 9/015* (2006.01)
*F24F 3/16* (2006.01)
(Continued)

(52) U.S. Cl.
CPC .............. *G06Q 30/01* (2013.01); *A61L 9/015* (2013.01); *A63J 5/00* (2013.01); *A63J 25/00* (2013.01); *F24F 3/166* (2013.01); *G05B 15/02* (2013.01); *G05B 19/048* (2013.01); *A61L 2209/111* (2013.01); *A63J 2005/008* (2013.01);
(Continued)

(58) Field of Classification Search
CPC ................... G06Q 30/01; G05B 19/048; G05B 2219/2642; A61L 9/015; F24F 3/166; F24F 2003/1689
See application file for complete search history.

(56) References Cited

U.S. PATENT DOCUMENTS 5,481,965 A * 1/1996 Kronman ............ A47J 37/0704
126/25 R
5,656,315 A * 8/1997 Tucker .................... A23L 27/70
426/293

(Continued)

FOREIGN PATENT DOCUMENTS

EP    2369900 A1    9/2011

OTHER PUBLICATIONS

ISR for PCT/IL2015/050394 (dated Aug. 9, 2015).

*Primary Examiner* — Adam Lee
(74) *Attorney, Agent, or Firm* — Koffsky Schwalb LLC; Mark I. Koffsky

(57) ABSTRACT

A computer implemented method, a computerized system and a computer program product for selective scent dispensing. The computer implemented method comprising: detecting an event, wherein the event is associated with a person entering a predetermined physical area; in response to the detection of the event, determining, by a processor, a scent for the event; and applying, by a dispenser, the scent on the predetermined physical area.

21 Claims, 4 Drawing Sheets

(51) Int. Cl.
*G05B 19/048* (2006.01)
*A63J 5/00* (2006.01)
*A63J 25/00* (2009.01)

(52) U.S. Cl.
CPC ............... *F24F 2003/1689* (2013.01); *G05B 2219/2642* (2013.01)

(56) References Cited

U.S. PATENT DOCUMENTS

| | | | |
|---|---|---|---|
| 6,199,549 B1* | 3/2001 | Yerkes | F24B 1/207 126/276 |
| 2002/0130146 A1* | 9/2002 | Borut | A61L 9/12 222/645 |
| 2004/0231360 A1* | 11/2004 | Lagardere | A44C 1/00 63/1.13 |
| 2005/0262883 A1* | 12/2005 | Yang | D06F 39/00 68/12.01 |
| 2006/0191319 A1* | 8/2006 | Kurup | G01N 33/24 73/23.34 |
| 2006/0196966 A1* | 9/2006 | Cheng | A47G 19/2205 239/60 |
| 2007/0145074 A1* | 6/2007 | Sevcik | B67D 1/06 222/129.1 |
| 2007/0159641 A1* | 7/2007 | Liccini | G09F 5/04 358/1.1 |
| 2007/0256572 A1* | 11/2007 | Davis | A47J 37/0786 99/482 |
| 2008/0279730 A1* | 11/2008 | Triplett | A01M 1/2033 422/123 |
| 2009/0006286 A1* | 1/2009 | Angell | G06K 9/00771 706/12 |
| 2009/0053383 A1* | 2/2009 | Endo | A23F 3/34 426/597 |
| 2009/0202446 A1* | 8/2009 | Vlad | A61L 9/012 424/45 |
| 2009/0311393 A1* | 12/2009 | Estess | A23B 4/044 426/312 |
| 2010/0258107 A1* | 10/2010 | Davidson | F24B 1/207 126/276 |
| 2011/0004986 A1* | 1/2011 | Vu | E03D 9/007 4/223 |
| 2011/0158919 A1* | 6/2011 | Kennison | A23F 3/163 424/55 |
| 2011/0189108 A1* | 8/2011 | Backes | A23L 1/236 424/49 |
| 2011/0226864 A1 | 9/2011 | Samsung | |
| 2011/0268605 A1 | 11/2011 | Scentcom | |
| 2012/0116915 A1* | 5/2012 | Zheng | G06Q 30/02 705/26.7 |
| 2013/0011523 A1* | 1/2013 | Belzowski | A23P 30/00 426/89 |
| 2013/0011525 A1* | 1/2013 | Belzowski | A23P 20/18 426/107 |
| 2013/0124365 A1* | 5/2013 | Pradeep | G06Q 30/06 705/26.43 |
| 2013/0191393 A1* | 7/2013 | Ji | G06Q 50/01 707/737 |
| 2014/0039684 A1 | 2/2014 | Van De Sluis et al. | |
| 2014/0060150 A1* | 3/2014 | Shaw | H04W 4/21 73/23.34 |
| 2014/0081682 A1* | 3/2014 | Perlmuter | G06Q 30/0601 705/7.11 |
| 2014/0121594 A1* | 5/2014 | Connor | A61F 5/0006 604/77 |
| 2014/0150669 A1* | 6/2014 | Green | B67D 1/0058 99/323.2 |
| 2014/0316881 A1* | 10/2014 | Movellan | G06K 9/00315 705/14.42 |
| 2014/0349256 A1* | 11/2014 | Connor | G09B 19/0092 434/127 |
| 2015/0019029 A1* | 1/2015 | Chandler | A61L 9/035 700/283 |
| 2015/0136109 A1* | 5/2015 | Baker | F24B 1/08 126/11 |
| 2015/0144012 A1* | 5/2015 | Frybarger | G06Q 30/0241 100/102 |
| 2015/0264892 A1* | 9/2015 | Nir | A01K 15/02 119/795 |
| 2017/0098121 A1* | 4/2017 | Ur | G06K 9/00288 |

* cited by examiner

US 10,078,842 B2

SELECTIVE SCENT DISPENSING

CROSS-REFERENCE TO RELATED APPLICATION

This application claims the benefit of Israeli Patent Application No. 231687 filed Mar. 24, 2014, entitled "SELECTIVE SCENT DISPENSING", which is hereby incorporated by reference in its entirety for all purposes.

TECHNICAL FIELD

The present disclosure relates to scent dispensers.

BACKGROUND

Smell is one of the strongest and most primal of all the human senses. Many researches shows that smell can influence human thoughts and behavior more than expected. Just like verbal, dress and physical cues, scent, may help people to convey impression and sometimes influence the way people perceive each other.

In perfumery, notes are descriptors of scents. Notes are generally separated into three classes: top notes, middle notes and base notes. The classes denote groups of scents that may be smelled with respect to the time after the perfume application. A top note scent may be a scent that is perceived immediately or within a short time after application of a perfume. A top note scent may typically consist of relatively small and light molecules. The top note may be characterized by a relatively noticeable scent. The top note may be of high volatility (e.g., evaporation coefficient of about 1 to about 14). The top note may be fast evaporating, such as within approximately seconds of dispensing. The top note may be suitable for conveying a desired initial impression to others.

The perfume industry is pushing the wealth of the scent world to practically every aspect of everyday life and successfully spreading into hospitality, retail, consumer packaged goods, beauty, healthcare, real estate food and accommodation.

Emerging scent applications, such as digitally transmitting and receiving scent, are becoming more affordable and therefore more available in the consumer marketplace. For example delivering a specific scent for enhancing videogame experience. Artificial recreation of a smell by synthesizing chemical molecules is one enabling technology of these scents on demand applications.

BRIEF SUMMARY

One exemplary embodiment of the disclosed subject matter is a method comprising: detecting an event, wherein the event is associated with a person entering a predetermined physical area; in response to the event, determining, by a processor, a scent for the event; and applying the scent on the predetermined physical area.

Another exemplary embodiment of the disclosed subject matter is a system comprising: a detecting component configured to detect an event associated with a person entering a predetermined physical area; a scent determinator configured to determine a scent for the event; and a dispenser configured to apply the scent on the predetermined physical area.

Yet another exemplary embodiment of the disclosed subject matter is a method comprising: automatically recognizing a food content about to be consumed by a person; determining, by a processor, a scent associated with the food content; and is automatically applying the scent on the person.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
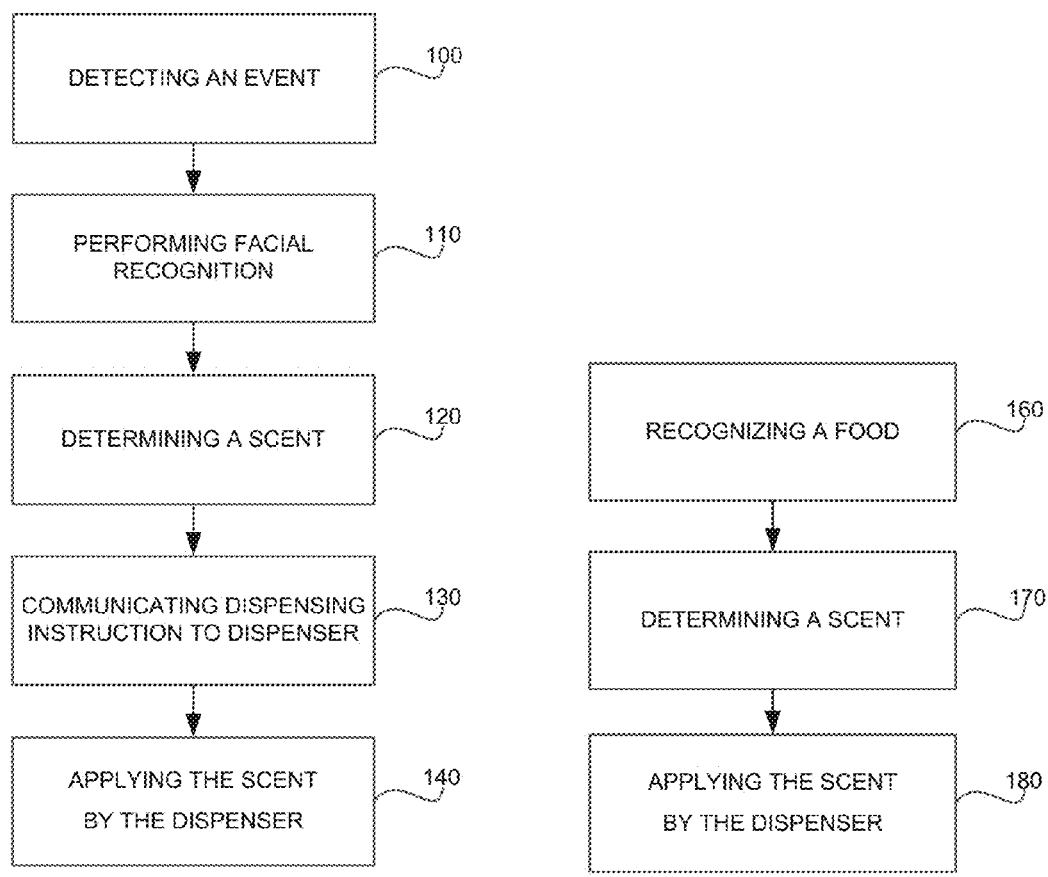
FIG. 1A shows a flowchart diagram of a method, in accordance with some exemplary embodiments of the disclosed subject matter.
FIG. 1B shows a flowchart diagram of a method, in accordance with some exemplary embodiments of the disclosed subject matter.

One technical problem dealt with by the disclosed subject matter, is to automatically personalize a scent to a person based upon characterization of the person and an event associated with commercial purposes. Business, such as for example, in the field of hospitality, retail, beauty, healthcare, real estate, dining, entertainment, or the like, may wish to utilize scent in their sales promotion methods or order to enhance their clients' experience. As an example, such businesses may wish to encourage a customer to evaluate specific goods, by exposing the customer to a specific scent that is expected to promote such behavior. To do so, business may need to adjust the scent for different people, for different purposes, in different locations (or areas), and at different business hours. Additionally or alternatively, an automatic and efficient manner to personalize a scent in a point of sale may also be desired in view of the growing awareness of the impact smell has on people's behavior.

One technical solution is determining an appropriate scent for an event that is associated with a person and applying the scent on the person. In some exemplary embodiments, facial recognition may be employed to allow personalization of the scent based on identity or other characteristics of a person. The disclosed subject matter may utilize a dispenser, capable of applying the appropriate scent for the event.

An event may be, for example, a person (e.g., customer) entering a predetermined physical area, such as crossing an aisle in the store, entering the store, or the like. Another example of an event may be a person eating in a restaurant or a person about to consume a food content.

In some exemplary embodiments, the scent may be selected based on different parameters, such as but not limited to characterization of the person (e.g., a gender of the person, an identity of the person, an age of the person, a demographic profile of the person, or the like); location of the person; time of a day; purchase history and customer profile of the person; a combination thereof; or the like.

In some embodiments, the disclosed subject matter may recognize an approaching person to a predetermined physical area and utilize a facial recognition module to characterize the approaching person. A scent can be selected and applied to the predetermined physical area shortly before the arrival of the person to the area. In some exemplary embodiments, the timing in which the scent is applied may be based upon the distance and the movement direction of the approaching person. Additionally or alternatively, the scent may be applied based on a gesture or a verbal greeting between the business representative and the approaching person.

In some embodiments, the dispenser may be a fast release dispenser. In some embodiments, the dispenser may be a fast release dispenser configured to apply a specific perfume from a plurality of perfume cartridges. Each one of the perfume cartridges may be associated with specific event. Additionally or alternatively, the dispenser may be operatively coupled to a scent synthesizer configured to synthesize a scent on-demand.

In some exemplary embodiments, the dispenser may dispense fast evaporating perfume which may evaporate relatively fast and will not interfere with another scent, should it be applied later on. Fast evaporating perfume may enable use of the disclosed subject matter to provide personalized scent for one person and to provide a different scent shortly thereafter for another person.

One technical effect of utilizing the disclosed subject matter is equipping businesses with an automatic scent system capable to impact the shopping experience of their customers. In some exemplary embodiments, utilizing systems of the disclosed subject matter may reform the way of doing businesses by enabling a personalized marketing approach that is scent-based.

Another technical effect of utilizing the disclosed subject matter is providing retail businesses, with automatic scent selecting system for improving the performance of sales personnel. Upon characterizing the customer's profile, such as types of items the customer purchases, purchasing habits, or the like, an appropriate scent may be applied to a predetermined area when the customer is present in that area. The scent may be selected so as to improve the probability that the customer will purchase any item or specific items. As an example, different scents may be used to convey different messages to the customer, such as one scent may be used to increase the reliability of the salesperson, another scent may be used to encourage purchase of more luxurious items, and yet another scent may increase the customer's desire to purchase specific items or services. The selected scent may convey any desired message which may have a business value when the customer is exposed to it, affected by it, or the like.

Referring now to FIG. 1A, showing a flowchart diagram of a method in accordance with some exemplary embodiments of the disclosed subject matter.

In Step 100, an event may be detected. The event may be used to trigger the system to select a specific scent for a person and apply the scent. A detecting component, such as 220 of FIG. 2, may be utilized to detect the event. In some exemplary embodiments, the event may be a person entering or approaching a predetermined physical area or otherwise associated with the predetermined physical area. In some exemplary embodiments, the event may be an activity of the person, such as, for example, eating, drinking, smoking, shopping, or the like.

In Step 110, facial recognition may be performed. The facial recognition may be performed by a facial recognition component, such as 230 of FIG. 2, which may be operatively coupled with a camera, such as 252 of FIG. 2. The facial recognition may determine one or more characterizations of a person, such as a gender of the person, an identity of the person, an age of the person, a demographic profile of the person, a combination thereof, or the like. Additionally or alternatively, the person may be a customer, and the facial recognition may characterize the customer based on a data repository comprising purchase history which may be used to determine a customer profile for the customer. In some exemplary embodiments, the event may not relate to any given person but rather to specific people or people having specific characteristics. Facial recognition may be utilized to characterize the person in order to detect the event in Step 100.

Additionally or alternatively image processing may be utilized to detect an approaching person and estimate his or her expected arrival time to the predetermined physical area based on the distance and direction.

In Step 120, a scent may be determined. The scent may be determined by a scent determinator, such as 240 of FIG. 2. The determination of the scent may be based on predefined rules. As an example, the rules may define a different scent in response to: different event types, different characterization of people, different purchasing habits of a customer, or the like.

Figure 2:
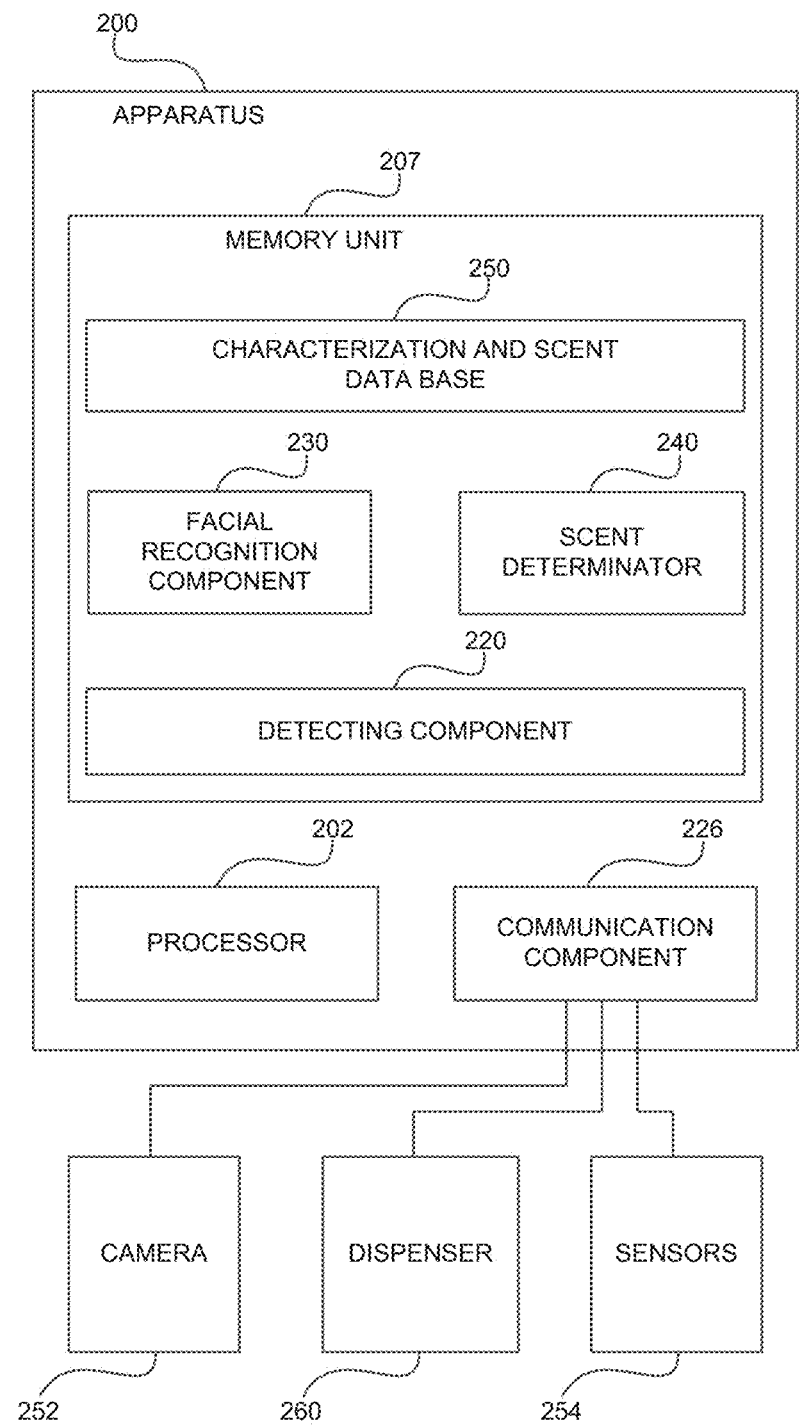
FIG. 2 shows a block diagram of a system, in accordance with some exemplary embodiments of the disclosed subject matter.

In some exemplary embodiments, the scent determination may be based on a characterization and scent database, such as 250 of FIG. 2. The database may comprise a set of rules associating the scent to an event type or properties thereof. As an example, the rules for a customer stepping into a predetermined area in a department store may define: a first scent to be selected in response to characterizing the customer as a man estimated as shopping for hardware tools; a second scent to be selected in response to characterizing the customer as a woman estimated as shopping for cosmetics, and a third scent to be selected for any person on a calendar event such as "Black Friday". In some exemplary embodiments, the scent determination may be based the type of food content the customer is eating. The food content may be any substance consumed to provide nutritional support for the body, including solid food content, liquid food content, or the like. In some exemplary embodiments, the food content may be an appetizer, a beverage, a dessert, a main course, a side dish, or the like.

In some exemplary embodiments, the determination of Step 120 may result in a selection of a specific scent to be applied in response to the event. Additionally or alternatively, Step 120 may determine a duration in which the scent is to be dispensed.

In some exemplary embodiments, the determined scent may be selected based on availability of perfumes. As an example, in case a perfume cartridge is depleted a replacement scent may be used instead.

In some exemplary embodiments, the determined scent may be a top note. The scent may be selected from available top note scents or from potentially synthesizable top note scents.

In Step 130, dispensing instruction may be communicated to a dispenser, such as 240 of FIG. 2. The instruction may indicate the selected scent of Step 120. In some exemplary embodiments, information may be communicated in addition to the selected scent, such as for example, a dispensing duration, an instruction to synthesize the scent, an instruction to apply the scent, a duty cycle of reapplying the scent, or the like. The communicated instruction may be communicated via wired communication, wireless communication, or the like.

In Step 140, the scent may be applied by a dispenser. In some exemplary embodiments, the dispenser may apply a fast evaporating scent towards the predetermined physical area, towards the person or his surround, or the like. In some exemplary embodiments, the dispenser may be configured to perform real time synthesis of the selected scent. In some embodiments, the dispenser may be configured to apply a specific perfume from a plurality of perfume cartridges. Each one of the perfume cartridges may be associated with specific event.

Referring now to FIG. 1B, showing a flowchart diagram of a method in accordance with some exemplary embodiments of the disclosed subject matter.

In Step 160, food content may be automatically recognized. The automatic recognition may utilize a camera, such as 252 of FIG. 2. The automatic recognition of the food content may utilize image processing methods. In some exemplary embodiments, the recognition may be based on matching an image of the food captured by the camera and comparing it against images of food items. The images may be a-priori provided. In some exemplary embodiments, images may be provided for each food item listed in a menu of a restaurant or food vendor at which the camera is overlooking. In some exemplary embodiments, the images of the food items listed in the menu may be stored in a data repository.

In Step 170, a scent may be determined. The scent determination may be performed by a scent determinator, such as 240 of FIG. 2. The determination of the scent may be performed by selecting a scent that is associated with the recognized food content. In some exemplary embodiments, each food content in the menu may be a-priori associated with a scent. In some exemplary embodiments, a different scent may be selected for a different food item. For example a couple having a dinner meal in restaurant may each receive a different scent as one may have a poultry dish while the other is eating vegetarian food. In some exemplary embodiments, the selected scent is expected to enhance a gastronomical experience of the person from the food content. As an example, the scent may enhance the flavor of the food. As another example, the scent may contradict the expected scent of the food content thereby creating for the user a cognitive dissonance. As yet another example, the scent may be adapted to contradict a displeasing after taste from consuming the food content. The scent may be selected to achieve other enhancements of the gastronomical experience than the examples listed above.

In Step 180, the scent may be applied by a dispenser in a similar manner to Step 140. It will be noted that dispensing instruction may be communicated in order to instruct the dispenser to apply the scent.

Referring now to FIG. 2, showing a block diagram of a system in accordance with some exemplary embodiments of the disclosed subject matter. An Apparatus 200 may be a computerized apparatus adapted to perform methods such as depicted in FIGS. 1A and 1B.

In some exemplary embodiments, Apparatus 200 may comprise a Processor 202. Processor 202 may be a Central Processing Unit (CPU), a microprocessor, an electronic circuit, an Integrated Circuit (IC) or the like. Additionally or alternatively, Apparatus 200 can be implemented as firmware written for or ported to a specific processor such as Digital Signal Processor (DSP) or microcontrollers, or can be implemented as hardware or configurable hardware such as field programmable gate array (FPGA) or application specific integrated circuit (ASIC). Processor 202 may be utilized to perform computations required by Apparatus 200 or any of it subcomponents.

In some exemplary embodiments of the disclosed subject matter, Apparatus 200 may comprise a Communication Component 226. Apparatus 200 may utilize Communication Component 226 as an interface to transmit and/or receive information and instructions between Apparatus 200 and external I/O devices, such as a Dispenser 260, Camera 252, Sensors 254 or the like. In some exemplary embodiments, the physical media used to transmit and receive the information may be: by wire (e.g., CAT-5), wireless (e.g., Wi-Fi) a combination thereof, or the like.

In some exemplary embodiments, Apparatus 200 may comprise a Memory Unit 207. Memory Unit 207 may be persistent or volatile. For example, Memory Unit 207 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, Memory Unit 207 may retain program code to activate Processor 202 to perform acts associated with any of the steps shown in FIG. 1A and/or 1B.

The components detailed below may be implemented as one or more sets of interrelated computer instructions, executed for example by Processor 202 or by another processor. The components may be arranged as one or more executable files, dynamic libraries, static libraries, methods, functions, services, or the like, programmed in any programming language and under any computing environment.

A Detecting Component 220 may be configured to detect an event associated with a person, such as for example, depicted in Step 100 of FIG. 1A. Additionally or alternatively, Detecting Component 220 may be configured to detect an event associated with a food content being consumed or about to be consumed by a person, such as exemplified in FIG. 1B. In some exemplary embodiments, the Detecting Component 220 may be operatively coupled with Sensors 254, Camera 252, a combination thereof, or the like.

A Facial Recognition Component 230 may be configured to perform facial recognition, such as for example, depicted in Step 110 of FIG. 1A. The Facial Recognition Component 230 may be operatively coupled with Camera 252. In some exemplary embodiments, Facial Recognition Component 230 may be utilized to characterize a person. A person may be characterized by gender, identity, age, demographic profile, a combination thereof, or the like. Additionally or alternatively, Facial Recognition Component 230 may be utilized in detecting an event of a person approaching the predetermined physical area.

In the present disclosure, the term "facial recognition" should be understood as a recognition of physical traits of persons or objects based on image processing. Facial recognition may include identifying a person, extracting physical features of a person captured in an image, or the like. The physical features may be, for example, facial features or non-facial features. In some exemplary embodiments, Facial Recognition Module 230 may be utilized to extract a physical feature of an age, based on a size of the person (e.g., potentially differentiating children from adults). As another example, Facial Recognition Module 230 may identify food content captured in an image, identifying a person entering or exiting a frame or an area within the frame, or the like.

A Scent Determinator 240 may be configured to determine the scent, such as for example, depicted in Step 120 of FIG. 1A or Step 170 of FIG. 1B. In some exemplary embodiments, Scent Determinator 240 may obtain event information from Detecting Component 220, characterization information from Facial Recognition Component 230, a combination thereof, or the like. In some exemplary embodiments, Scent Determinator 240 may utilize a Characterization and Scent Data Base (CSDB) 250 to determine the scent based on the event and characterization information. Additionally or alternatively, the Scent Determinator 240 may instruct a dispenser such as Dispenser 260 to apply the selected scent on the person.

Memory Unit 207 may retain a CSDB 250. In some exemplary embodiments, the CSDB 250 may be a database which comprises rules for scent selection. The rules may define a scent to be selected based on event properties, based on characterization of a target person, or the like. In some exemplary embodiments, Scent Determinator 240 may utilize CSDB 250 for determining the scent. The determination of the scent may be based on predefined rules that are retained in CSDB 250. As an example, the rules may define a different scent in response to: different event types, different characterization of people, different purchasing habits of customers, different food served in a restaurant, or the like.

As an example, CSDB 250 may retain a record corresponding to a rule of selecting SCENT#1 for a person characterized as a young woman most likely to buy fashion items. Another record corresponding to a rule of selecting SCENT#5 for a person characterized as man, most likely to buy hardware tools. CSDB 250 may also retain a record corresponding to a rule of selecting, for example, SCENT #3 associated with date such as for example "St. Patrick's Day".

In accordance with some exemplary embodiments of the disclosed subject matter, a Camera 252 may be utilized for performing facial recognition of a person. In some exemplary embodiments, Camera 252 may be positioned in a location facilitating clear field of view for capturing the face a person present in the predetermined physical area or approaching thereto. In some exemplary embodiments, one or more cameras such as Camera 252 may be used to cover the predetermined physical area. Additionally or alternatively, one camera such as Camera 252 may be used to cover one or more predetermined physical areas, such as for example, Camera 321 of FIG. 3.

In some exemplary embodiments of the disclosed subject matter, Sensors 254 may be utilized by Detecting Component 220 for detecting an event. In some exemplary embodiments, Sensors 254 may be used to detect an event of a person entering a predetermined physical area. In some exemplary embodiments, Sensors 254 may be positioned in a location adequate for monitoring the predetermined physical areas. In some exemplary embodiments, one or more sensors may be utilized for one or more predetermined physical areas.

In some exemplary embodiments, Sensors 254 may comprise any or all of the following: a proximity sensor, a motion detector, a combination thereof, or the like. In some exemplary embodiments, Sensors 254 may be configured to detect a movement of hands, head, or other parts of the person's body to indicate an event, for example, a person eating, such as, Person 401 of FIG. 4.

In some exemplary embodiments, Sensors 254 may comprise a scent sensor. The scent sensor may be a device capable of recognizing a smell. The scent sensor may be utilized to identify an event upon recognition of a specific smell such as for example a smell of cigarettes smoke, or the like. In some exemplary embodiments, based the scent may be determined so as to contradict a foul odor, to provide optimal results in view of present odor at the physical area, or the like.

In some exemplary embodiments of the disclosed subject matter, a Dispenser 260 may be used. Dispenser 260 may be a fast release dispenser. Dispenser 260 may be utilized to perform Step 140 of FIG. 1A or Step 180 of FIG. 1B. In some exemplary embodiments, Dispenser 260 may receive instruction to apply a scent from the Scent Determinator 240 through Communication Component 226. In some exemplary embodiments, the instruction may include the selected scent to be applied. In some exemplary embodiments, Dispenser 260 may comprise a scent synthesizer for synthesizing the selected scent on demand. In some embodiments, the dispenser may comprise a plurality of perfume cartridges, wherein Dispenser 260 may apply the perfume from the cartridge associated with the event. In some exemplary embodiments, Dispenser 260 may be physically separated from Apparatus 200 and may be positioned in proximity to the predetermined physical area.

In some exemplary embodiments, scents of top note class may be used by Dispenser 260. Top note scents may be perceived right after application of the perfume. Top note scents may typically consist of small and light molecules and may be characterized by noticeable scent, volatility and fast evaporation. Top note scents may be used to convey a desired impression. In some exemplary embodiments, as the top note scents may evaporate relatively fast, application of another scent that may occur within several minutes or even dozen of seconds, would not be disturbed by the previously applied top note scent.

Figure 3:
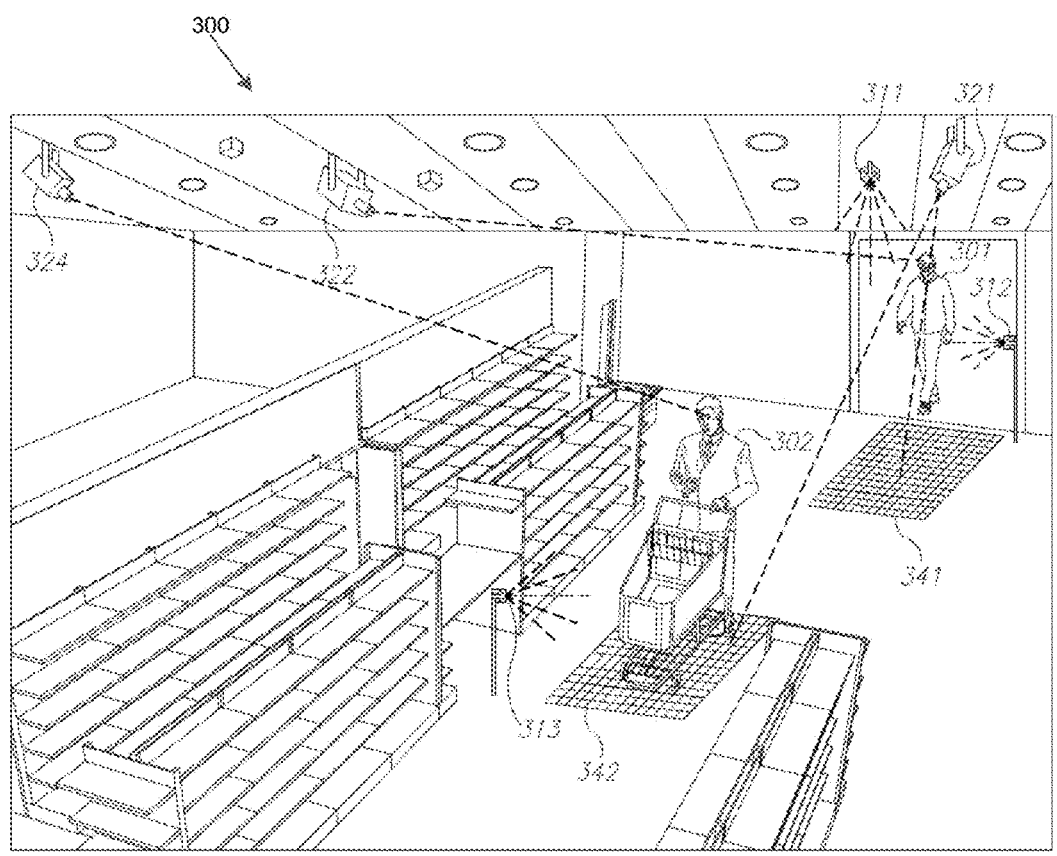
FIG. 3 shows an illustration of a store, in accordance with some exemplary embodiments of the disclosed subject matter.

Referring now to FIG. 3, showing an illustration of a store, in accordance with some exemplary embodiments of the disclosed subject matter.

In some exemplary embodiments, a system may be deployed in a Store 300. The system deployed in Store 300 may comprise: an apparatus, such as Apparatus 200 of FIG. 2 (not shown); Dispensers 311, 312 and 313 and Cameras 321, 322 and 313.

In some exemplary embodiments, Cameras 321 and 322 may be associated with Predetermined Physical Area (PPA) 341. Cameras 321 and 322 be utilized to detect an event of Customer 301 entering Predetermined Physical Area (PPA) 341. In response to a detection of the event, the Facial Recognition Component 230 of FIG. 2 may utilize the images provides by Cameras 321 and 322 to perform facial recognition of Customer 301 present in PPA 341. In some exemplary embodiments, Scent Determinator 240 of FIG. 2 may determine a scent based various parameters associated with the event, such as the characterization of Customer 301. Additionally or alternatively, the Scent Determinator 240 of FIG. 2 may instruct Dispenser 312 to apply the selected Scent 352 towards PPA 341 so as to expose Customer 301 to Scent 352.

In some exemplary embodiments, an event may occur upon the identification of Customer 302 approaching PPA 342. The identification may be performed, for example, by Facial Recognition Component 230 operatively coupled with Camera 324. In some exemplary embodiments, Customer 302 may be identified as a returning customer characterized as a "bargain seeker". In some exemplary embodiments, Scent Determinator 240 may instruct Dispenser 313 to apply scent associated with today's bargain product.

In some exemplary embodiments, Scent Determinator 240 may instruct Dispenser 311 to apply a scent associated with the a holiday sale product during a holiday shopping season, on each customer stepping in PPA 341, or on each customer that meets a certain criterion.

Figure 4:
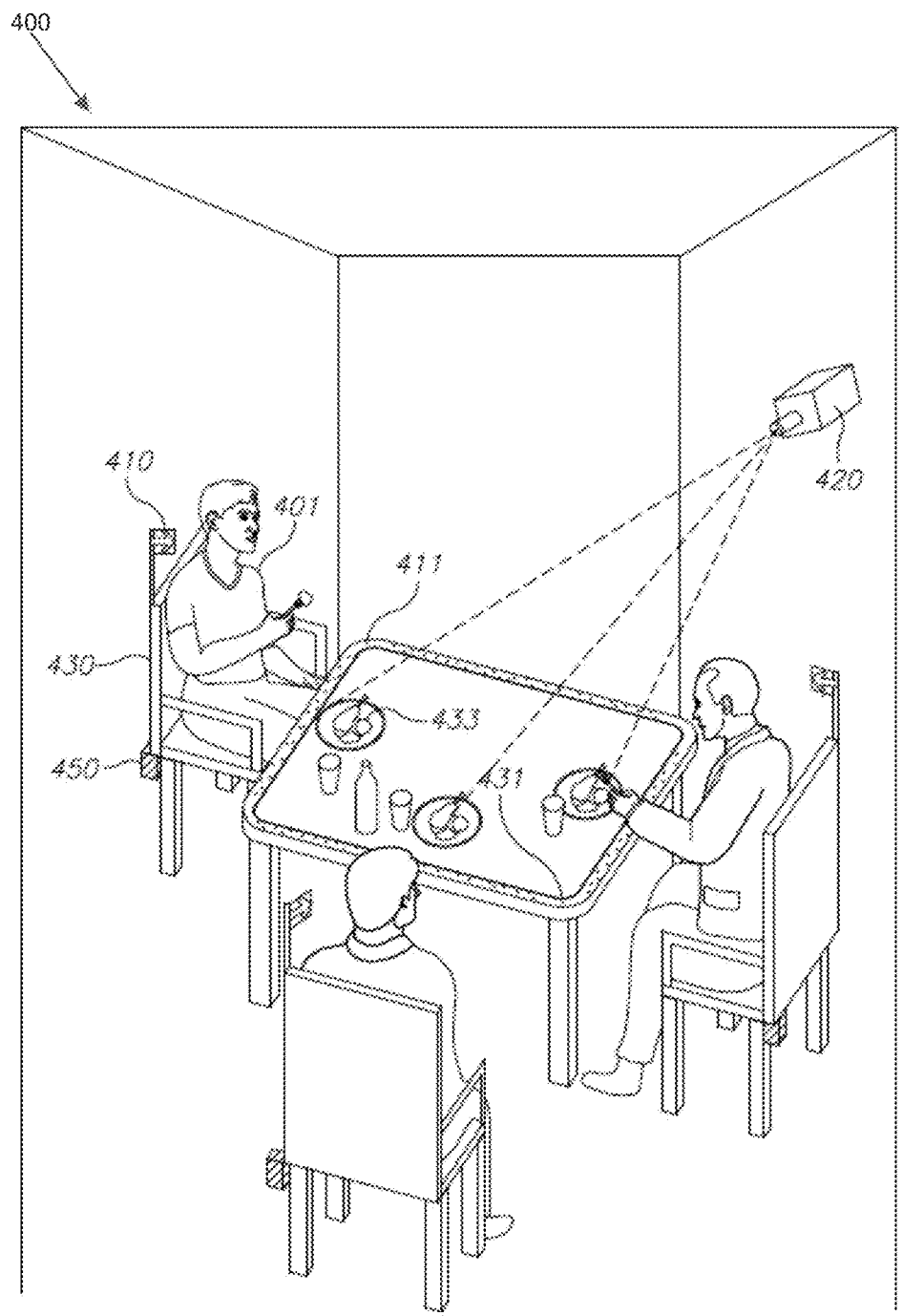
FIG. 4 shows an illustration of a restaurant, in accordance with some exemplary embodiments of the disclosed subject matter.

Referring now to FIG. 4, showing a restaurant, in accordance with some exemplary embodiments of the disclosed subject matter.

In some exemplary embodiments, a system may be deployed, for example in a restaurant, such as Restaurant 400. The system deployed in Restaurant 400 may comprise: an apparatus such as Apparatus 200 of FIG. 2 (not shown); Dispensers 410 and 411; Sensor 450, such as a proximity sensor, weight sensor, or the like, and a Camera 420.

In some exemplary embodiments, the apparatus of the system deployed in Restaurant 400 may determine, upon an indication from Sensor 450, that a person, such as Customer 401, is sitting on a Chair 430 at a Table 431 and that the person may be consuming or about to consume food content located on a Dish 433. Following the determination, the apparatus may execute an automatic sequence of operations comprising Steps 160, 170 and 180 of FIG. 1B. The automatic sequence may be concluded by applying a selected scent at Customer 401 to enhance his or her gastronomical experience while consuming the food content.

In some exemplary embodiments, the selected scent is expected to enhance the gastronomical experience of one or more people sitting, for example, at Table 431. Each person having a meal may receive a scent associated to the food content he or she consumes. In some exemplary embodiments, the expected scent may enhance the gastronomical experience by emphasizing the flavor of the food, by contradicting the expected scent of the food, by eliminating after taste from consuming the food, by creating an aura reminding of a place associated with the food (e.g., pine forest scent for Christmas meal), a combination thereof, or the like.

In some exemplary embodiments, Camera 420 may be utilized in Step 160 to perform food content recognition of the food content served in Dish 433. Following the recognition, Step 170 may be performed to select a scent associated with the food content in Dish 433. In some exemplary embodiments, the recognition comprises matching a captured image of the food content (by Camera 420) against images of the menu items of Restaurant 400. In some exemplary embodiments, the menu may be stored in a data repository, such as CSDB 250 of FIG. 2. The menu may comprise images of the food items, each of which may have a specific scent associated thereto. Following the scent selection, Step 180 may be preformed to apply the scent. The selected scent may be applied by Dispenser 411 and/or Dispenser 410 to Customer 401.

In some exemplary embodiments, the system may be configured to apply the scent at a time associated with Customer 401 consuming the food content. As an example, Dispenser 410 may dispense a scent at a timing in which Customer 401 tastes the food content, picks a silverware to consume the food content, draws the food content near the mouth or nose of Customer 401, or the like.

In some exemplary embodiments, one or more dispenser may be utilized. In one embodiment, a dispenser may be mounted on a chair and positioned so as to apply the scent on a person sitting on the chair. Additionally or alternatively, a dispenser may be mounted on a table and be configured to apply the scent to a person sitting next to the table. Additionally or alternatively, a dispenser may be mobile and may be manually positioned on the table, such as by a waiter. Additionally or alternatively, the dispenser may be embedded within a plate or other dishware used to serve the food content.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   detecting an event, wherein the event is a first person entering a predetermined physical area (PPA), wherein a dispenser is located within the PPA and is permanently associated therewith so as to be capable of applying a scent to be sensed by the first person located within the PPA;
   in response to detecting the event, determining, by a processor, a scent for the event based on a time of day of the detecting and an interaction between the first person and a second person within the PPA; and
   applying the scent, using the dispenser, on the PPA based on a movement direction of the first person within the PPA.

2. The method of claim 1, wherein said determining further comprises performing facial recognition of the first person to characterize the first person, wherein the scent is further determined based on the characterization of the first person.

3. The method of claim 2, wherein the characterization is selected from the group consisting of: a gender of the first person; an identity of the first person; an age of the first person and a demographic profile of the first person.

4. The method of claim 1, wherein the first person is a customer, wherein said determining is further performed based on a customer profile of the customer, wherein the customer profile is based on a purchase history of the customer, wherein the purchase history is retained in a data repository, and whereby the scent is further determined based on the purchase history of the customer entering the PPA.

5. The method of claim 1, wherein said detecting the event further comprises performing facial recognition to characterize the first person, wherein the scent is further determined based on the characterization of the person.

6. The method of claim 1, wherein said applying comprises applying, the dispenser, a perfume having the scent.

7. The method of claim 6, wherein the perfume consists of a top note.

8. The method of claim 1, wherein said applying further comprises transmitting an instruction from an apparatus to the dispenser, wherein the dispenser is external to the apparatus; and in response to receiving the instruction, the dispenser applying the scent on the PPA.

9. The method of claim 1, wherein said applying the scent comprises applying a perfume having the scent, the perfume having an evaporating coefficient of between 1 and 14.

10. The method of claim 1 further comprising applying a third scent in response to a second event, wherein the first scent and the third scent are different, wherein the third scent and the second scent are different, and wherein the first scent is configured to evaporate without interfering with the third scent.

11. A system comprising:
    a detecting component configured to detect an event, wherein the event is a first person entering a predetermined physical area (PPA);
    a scent determinator configured to determine a scent for the event based on a time of day of when the detecting component detects the event and an interaction between the first person and a second person within the PPA; and
    a dispenser configured to apply the scent on the PPA based on a movement direction of the first person within the PPA, wherein said dispenser is located within the PPA and is permanently associated therewith so as to be capable of applying the scent to be sensed by the first person located within the PPA.

12. The system of claim 11, wherein said detecting component is operatively coupled with a camera, wherein said detecting the event further comprises performing facial recognition of the first person to characterize the first person.

13. The system of claim 11, wherein said system is operatively coupled with a camera, wherein the camera is physically positioned in a fixed location in which the camera is capable of observing the PPA.

14. The system of claim 11, wherein said scent determinator comprises a facial recognition component operatively coupled with a stationary camera, wherein said facial recognition component is configured to characterize the first person, wherein the scent is further determined based on the characterization of the first person.

15. The system of claim 11, wherein the first person is a customer, wherein said scent determinator is further configured to obtain a customer profile of the customer, wherein the customer profile is based on a purchase history of the customer, wherein the purchase history is retained in a data repository, and whereby the scent is further determined based on the purchase history of the customer entering the PPA.

16. The system of claim 11, wherein said dispenser is a stationary dispenser.

17. The system of claim 11 further comprising a second dispenser located within a second PPA, wherein the second dispenser is capable of applying a second scent to be sensed by a third person located within the second PPA.

18. A method comprising:
automatically recognizing a food content about to be consumed by a person, wherein the food content has one or more scents;
determining, by a processor, a particular scent associated with a type of the recognized food content, wherein the particular scent is different than the one or more scents of the food content; and
in response to the determining, automatically applying the particular scent on the person with a dispenser embedded within a plate used to serve the food content to the person when the person picks up the food content.

19. The method of claim 18, wherein the food content is selected from the group consisting of: an appetizer, a beverage, a dessert, a main course and a side dish.

20. The method of claim 18, wherein said recognizing comprises matching an image of the food content against images of menu items of a restaurant.

21. A dispenser,
wherein said dispenser is embedded within a plate used to serve food content to a person, wherein the food content has one or more scents; and
wherein said dispenser is configured to automatically apply a particular scent on the person when the person picks up the food content in response to a determination of the particular scent associated with a type of the food content, wherein the particular scent is different than the one or more scents of the food content.

* * * * *